(12) United States Patent
Suñé Negre et al.

(10) Patent No.: US 10,525,018 B2
(45) Date of Patent: Jan. 7, 2020

(54) CALCIFEDIOL SOFT CAPSULES

(71) Applicant: FAES FARMA, S.A., Leioa-Vizcaya (ES)

(72) Inventors: Josep María Suñé Negre, Barcelona (ES); Ignacio Ortega Azpitarte, Leioa-Vizcaya (ES); Pepa Del Arenal Barrios, Leioa-Vizcaya (ES); Gonzalo Hernández Herrero, Leioa-Vizcaya (ES)

(73) Assignee: FAES FARMA, S.A., Vizcaya (ES)

( * ) Notice: Subject to any disclaimer, the term of this patent is extended or adjusted under 35 U.S.C. 154(b) by 0 days.

(21) Appl. No.: 15/524,174

(22) PCT Filed: Feb. 5, 2016

(86) PCT No.: PCT/EP2016/052458
§ 371 (c)(1),
(2) Date: May 3, 2017

(87) PCT Pub. No.: WO2016/124724
PCT Pub. Date: Aug. 11, 2016

(65) Prior Publication Data
US 2017/0348249 A1 Dec. 7, 2017

(30) Foreign Application Priority Data

Feb. 6, 2015 (EP) .................................... 15382042

(51) Int. Cl.
*A61K 31/047* (2006.01)
*A61K 9/48* (2006.01)
*A61K 31/593* (2006.01)

(52) U.S. Cl.
CPC ............ *A61K 31/047* (2013.01); *A61K 9/485* (2013.01); *A61K 9/4825* (2013.01); *A61K 9/4833* (2013.01); *A61K 9/4858* (2013.01); *A61K 9/4866* (2013.01); *A61K 31/593* (2013.01)

(58) Field of Classification Search
CPC ............................. A61K 9/4825; A61K 31/593
See application file for complete search history.

(56) References Cited

U.S. PATENT DOCUMENTS

| 4,532,126 A | * | 7/1985 | Ebert ..................... A23G 3/368 424/456 |
| 4,997,824 A | | 3/1991 | Popovtzer et al. |
| 6,893,658 B1 | * | 5/2005 | Iida ....................... A61K 9/4858 424/456 |
| 8,501,717 B2 | * | 8/2013 | Zong ..................... A61K 31/593 424/684 |
| 2003/0158264 A1 | * | 8/2003 | Radhakrishnan .... A61K 9/4858 514/649 |
| 2007/0098819 A1 | * | 5/2007 | Thys-Jacobs .......... A61K 31/59 424/682 |
| 2011/0105444 A1 | | 5/2011 | Deluca et al. |
| 2015/0297529 A1 | * | 10/2015 | Spleiss ................. A61K 9/4825 424/456 |

FOREIGN PATENT DOCUMENTS

| EP | 0629405 A1 | 12/1994 |
| EP | 1208843 A1 | 5/2002 |
| JP | 04288016 A | 10/1992 |
| WO | 2007092755 A2 | 8/2007 |
| WO | 2008097646 A1 | 8/2008 |
| WO | 2008134512 A1 | 11/2008 |

OTHER PUBLICATIONS

AlfaD © Alpha D3 0.25, 0.5 or 1 microgram Capsules, "Alfacalcidol, Package Leaflet", Apr. 2010.
Alfarol © Capsules 3 µg, "Alfacalcidol, Package Leaflet", Mar. 2010.
Hectorol © Capsules, "Label, FDA", 2010.
Zemplar © Capsules, "Label, FDA", May 5, 2009.
Shieh, A., et al., "Effects of Cholecalciferol vs Calcifediol on Total and Free 25-Hydroxyvitamin D and Parathyroid Hormone", "J. Clin. Endocrinal Metab.", Apr. 2017, pp. 1133-1140, vol. 102, No. 4, Publisher: https://academic.oup.com/jcem.
Bergstrom, D.H., et al, "Capsules, Soft", "Encyclopedia of Pharmaceutical Technology, Third Edition", 2007, Pp. 419-430, vol. 1.

\* cited by examiner

*Primary Examiner* — Kyle A Purdy
(74) *Attorney, Agent, or Firm* — Hultquist, PLLC; Steven J. Hultquist

(57) ABSTRACT

The present invention relates to calcifediol soft capsules, to their use in the treatment or prevention of diseases related to vitamin D deficiency, such as vitamin D deficiency, demineralization such as hypocalcemia and hypophosphatemia, renal osteodystrophy, rickets, osteoporosis, osteopenia, osteoarthritis, osteoarthrosis, osteomalacia, hypoparathyroidism, and inflammatory bowel disease, and to their process of manufacture.

29 Claims, 1 Drawing Sheet

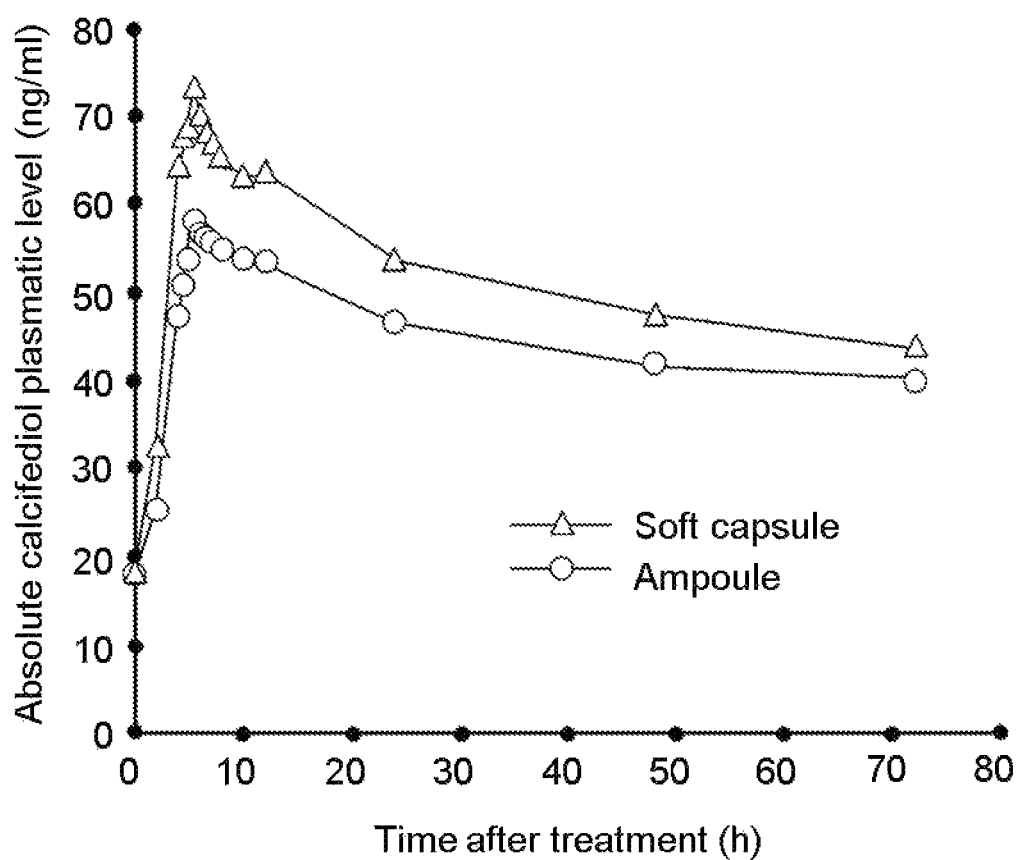

CALCIFEDIOL SOFT CAPSULES

CROSS-REFERENCE TO RELATED APPLICATIONS

This application is a U.S. national phase under the provisions of 35 U.S.C. § 371 of International Patent Application No. PCT/EP2016/052458 filed Feb. 5, 2016, which in turn claims priority of European Patent Application No. 15382042.8 filed Feb. 6, 2015. The disclosures of such international patent application and European priority patent application are hereby incorporated herein by reference in their respective entireties, for all purposes.

FIELD OF THE INVENTION

The present invention relates to calcifediol soft capsules, to their use in the treatment or prevention of diseases related to vitamin D deficiency, and to their process of manufacture.

STATE OF THE ART

Calcifediol, also known as calcidiol, 25-hydroxycholecalciferol, 25-hydroxyvitamin $D_3$ (abbreviated 25(OH)$D_3$) or (6R)-6-[(1R,3aR,4E,7aR)-4-[(2Z)-2-[(5S)-5-hydroxy-2-methylidene-cyclohexylidene]ethylidene]-7a-methyl-2,3,3a,5,6,7-hexahydro-1H-inden-1-yl]-2-methyl-heptan-2-ol, has the chemical structure shown below.

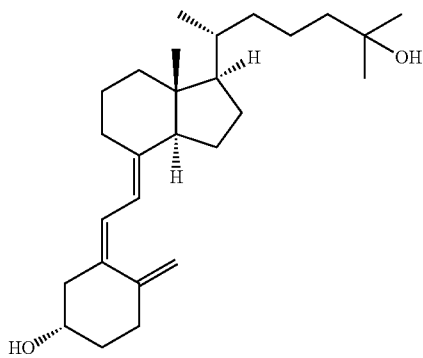 [SMILES: C=C1CC[C@H](O)C/C1=C/C=C1\CCC[C@]2(C)[C@@H]([C@H](C)CCCC(C)(C)O)CC[C@@H]12]

Calcifediol is used for the treatment of diseases related to vitamin D deficiency.

Calcifediol is highly lipophilic and has poor water solubility. Due to these physicochemical properties, it is difficult to formulate calcifediol in an immediate release pharmaceutical preparation for oral administration having suitable oral bioavailability.

Solubility, dissolution and gastrointestinal permeability are fundamental parameters that control rate and extent of drug absorption and its bioavailability. The water solubility of a drug is a fundamental property that plays an important role in the absorption of the drug after oral administration. Oral bioavailability of a drug depends on several parameters such as aqueous solubility, drug permeability, dissolution rate, first-pass metabolism and susceptibility to efflux mechanisms. However, for drugs having poor water solubility, the limiting factor to the in vivo bioavailability after oral administration are aqueous solubility and dissolution in the gastrointestinal fluids.

Thus, the type of pharmaceutical preparation that is administered orally has a direct influence on the bioavailability of poorly water-soluble drugs. In particular the bioavailability of orally administered preparations decreases in the following order: solutions>suspensions>emulsions>capsules>tablets>coated tablets.

Prior art immediate release calcifediol pharmaceutical preparations for oral administration having suitable bioavailability are those marketed under the name Hidroferol® (Faes Farma), wherein calcifediol is provided as a solution in a medium chain triglyceride and an antioxidant. One example of such a formulation is a solution consisting of calcifediol (0.266 mg; 15,960 IU calcifediol), medium chain triglycerides (1.5 ml) and α-tocopherol acetate (0.266; vitamin E acetate).

The oral bioavailability of some hydrophobic drugs, such as cyclosporine A (Gursoy, R. N., Benita, S., *Biomedicine Pharmacotherapy*, 2004, 58, 173-182) has been improved by using self-emulsifying drug delivery systems (SEDDS). These systems are isotropic mixtures of oils, surfactants, solvents and co-solvents/surfactants that rapidly and spontaneously form fine oil in water emulsions, microemulsions or nanoemulsions when introduced into aqueous phases under gentle agitation. Thus, SEDDS are readily dispersed in the gastrointestinal tract, where the motility of the stomach and small intestine provides the agitation necessary for emulsification. The efficiency of oral absorption of the drug compound from the SEDDS depends on many formulation-related parameters, such as surfactant concentration, oil/surfactant ratio, polarity of the emulsion, droplet size and charge, among others. Thus, only very specific pharmaceutical excipient combinations will lead to efficient self-emulsifying systems. Although many studies have been carried out, there are only few drug products that have been formulated as SEDDS (comprising the drug and a mixtures of oils, surfactants, solvents and co-solvents/surfactants) confirming the difficulty of formulation hydrophobic drug compounds into such formulations.

Other types of calcifediol oral formulations have been described, such as controlled release solid formulations comprising calcifediol (WO 2007/092755), wherein the active compound is provided within a wax matrix that releasably binds the drug. However, the presence of said wax or other components that releasably binds the drug does not allow the immediate release of calcifediol.

In view of the above, there is a need to find immediate release calcifediol solid oral formulations having improved bioavailability.

SUMMARY OF THE INVENTION

The authors of the present invention have found a calcifediol immediate release oral formulation having improved bioavailability with respect to a liquid calcifediol immediate release oral formulation of the prior art (i.e., Hidroferol®).

Therefore, according to a first aspect, the present invention is directed to a soft capsule comprising:
a) a soft capsule shell; and
b) a pharmaceutical composition comprising:
  calcifediol,
  an oily component selected from the group consisting of a medium chain triglyceride, isopropyl myristate, $C_{14}$-$C_{18}$ alkyl alcohol, a $C_{14}$-$C_{18}$ alkenyl alcohol, lanolin alcohol and mixtures thereof, and
  a pharmaceutically acceptable organic solvent selected from the group consisting of ethanol, isopropanol, propylene glycol, polyethylene glycol, benzyl alcohol and mixtures thereof;

wherein the soft capsule shell encapsulates the pharmaceutical composition and wherein said pharmaceutical composition is devoid of waxes.

According to a further aspect, the present invention is directed to a soft capsule as defined above, for use in medicine.

A further aspect of the invention is a soft capsule as defined above, for use in the treatment and/or prevention of a disease selected from the group consisting of vitamin D deficiency, demineralization such as hypocalcemia and hypophosphatemia, renal osteodystrophy, rickets, osteoporosis, osteopenia, osteoarthritis, osteoarthrosis, osteomalacia, hypoparathyroidism, and inflammatory bowel disease.

A further aspect of the invention is directed to the use of a soft capsule as defined above, in the manufacture of a medicament for the treatment and/or prevention of a disease selected from the group consisting of vitamin D deficiency, demineralization such as hypocalcemia and hypophosphatemia, renal osteodystrophy, rickets, osteoporosis, osteopenia, osteoarthritis, osteoarthrosis, osteomalacia, hypoparathyroidism, and inflammatory bowel disease.

In a further aspect, the invention is directed to a method of treatment and/or prevention of a disease selected from the group consisting of vitamin D deficiency, demineralization such as hypocalcemia and hypophosphatemia, renal osteodystrophy, rickets, osteoporosis, osteopenia, osteoarthritis, osteoarthrosis, osteomalacia, hypoparathyroidism, and inflammatory bowel disease, said method comprising administering to a patient in need of such a treatment a soft capsule as described above.

In a further aspect, the invention is directed to a process for preparing a soft capsule as defined above, said process comprising:
a) preparing a mixture comprising calcifediol; the oily component; and the pharmaceutically acceptable organic solvent; and optionally calcium ions, iron ions, vitamin B12, vitamin B9, levomefolic acid or a pharmaceutically acceptable salt thereof, an essential unsaturated fatty acid and/or a bisphosphonate;
b) preparing a mixture comprising gelatin; the plasticizer; water; and optionally a pharmaceutically acceptable opacifying agent and/or a pharmaceutically acceptable coloring agent;
c) forming a shell from the mixture of step b);
d) filling the shell with the mixture of step a), and
e) drying the capsule obtained in step d).

DESCRIPTION OF THE FIGURE

FIG. 1 shows the time-concentration plot obtained in Example 3, i.e. after administration of calcifediol soft capsules according to the invention (triangles) or the reference calcifediol ampoule (circles).

DETAILED DESCRIPTION OF THE INVENTION

In the context of the present invention, the following terms have the meaning detailed below:

The term "$AUC_{0-72}$" refers to the area under the curve (mathematically known as integral) in a plot of concentration of drug in blood plasma against time, starting at the time the drug is administered (0 hours) and ending after 72 hours.

The term "$C_{max}$" refers to the maximum (or peak) serum concentration that is achieved after administration of calcifediol.

The term "$C_{14}$-$C_{18}$ alkyl alcohol" refers to a linear or branched hydrocarbon chain radical consisting of carbon and hydrogen atoms, containing no insaturation, having between 14 and 18, carbon atoms and which is attached to a hydroxyl group (OH) by a single bond, including for example myristyl alcohol ($C_{14}$), cetyl alcohol ($C_{16}$), stearyl alcohol ($C_{18}$), cetostearyl alcohol (mixture of cetyl and stearyl alcohol as main components).

The term "$C_{14}$-$C_{18}$ alkenyl alcohol" refers to a linear or branched hydrocarbon chain radical consisting of carbon and hydrogen atoms, containing one, two or three unsaturations, having between 14 and 18, carbon atoms and which is attached to a hydroxyl group (OH) by a single bond, including for example oleyl alcohol ($C_{18}$).

The term "medium chain triglyceride" or "MCT" refers to triesters of glycerol and $C_6$-$C_{12}$ fatty acids, examples of said fatty acids being caproic acid ($C_6$), caprylic acid ($C_8$), capric acid ($C_{10}$) and lauric acid ($C_{12}$). The three fatty acids of the MCT can be the same or different, preferably there are two different fatty acids. Preferred medium chain triglycerides are caprylic/capric acid triglyceride (marketed as Miglyol® 812 or 810).

The term "essential unsaturated fatty acid" refers to straight a chain hydrocarbon possessing a carboxyl group at one end having one or more double bonds (C═C), preferably one, two, three, four, five or six double bonds, wherein the first double bond exists at the third carbon-carbon bond from the terminal $CH_3$ end of the carbon chain (omega-3 fatty acid), at the sixth carbon-carbon bond from the terminal $CH_3$ end of the carbon chain (omega-6 fatty acid), or at the ninth carbon-carbon bond from the terminal $CH_3$ end of the carbon chain (omega-9 fatty acid). Examples of essential unsaturated fatty acids are omega-3 fatty acids, such as α-linolenic acid (ALA), eicosapentaenoic acid (EPA), and docosahexaenoic acid (DHA), hexadecatrienoic acid (HTA), stearidonic acid (SDA), eicosatrienoic acid (ETE), eicosatetranoic acid (ETA), heneicosapentaenoic acid (HPA), docosapentaenic acid (DPA), tetracosapentaenoic acid and tetracosahexaenoic acid and mixtures thereof; omega-6 fatty acids, such as linoleic acid (LA), γ-linolenic acid (GLA), calendic acid, eicosadienoic acid, dihomo-γ-linolenic acid (DGLA), arachidonic acid (AA), docosadienoic acid, adrenic acid, docosapentaenoic acid, tetracosatetraenoic acid, tetracosapentaenoic acid, and mixtures thereof; omega-9 fatty acids, such as oleic acid, elaidic acid, gondoic acid, mead acid, erucic acid and nervonic acid, and mixtures thereof. Preferred omega-3 fatty acids are α-linolenic acid (ALA), eicosapentaenoic acid (EPA), docosahexaenoic acid (DHA) and mixtures thereof. Preferred omega-6 fatty acids are linoleic acid (LA), γ-linolenic acid (GLA), dihomo-γ-linolenic acid (DGLA), arachidonic acid (AA), and mixtures thereof. Preferred omega-9 fatty acids are oleic acid and erucic acid, still more preferably oleic acid.

The term "pharmaceutically acceptable" refers to molecular entities and compositions that are physiologically tolerable and do not typically produce an allergic or similar untoward reaction, such as gastric upset, dizziness and the like, when administered to a human or an animal. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "pharmaceutically acceptable salts" refers acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkyle-nethanolamine, triethanolamine, glucamine and basic aminoacids salts. Examples of the metallic salts include, for example, sodium, potassium, calcium, magnesium, aluminium and lithium salts.

The term "polyethylene glycol" or "PEG" refers to an oligomer or polymer of ethylene oxide with an average molecular weight of from 150 to 650 daltons, preferably from 150 to 550 daltons, more preferably from 150 to 450 daltons. The polyethylene glycols are also referred to as PEG followed by a number indicating its average molecular weight, for examples PEG 200 refers to a polyethylene glycol having an average molecular weight of 200 daltons. Preferred polyethylene glycols are PEG 200, PEG 400, and mixtures thereof; more preferably PEG200, PEG400, and mixtures thereof.

The term "soft capsule" is well known in the art and refers to a capsule having a soft capsule shell, as opposed to hard capsules that are made up of a rigid shell. A soft capsule shell is generally made of gelatin, water and plasticizer in various mixtures which gives elasticity and softness to the walls (shell). Soft capsules are usually formed in a single piece, as opposed to hard capsules that are made up of a shell in two pieces that fit together.

The term "surfactant" refers to compounds that are amphiphilic, i.e. they contain both hydrophobic groups (tail) and hydrophilic groups (head), therefore, a surfactant contains both a water insoluble (or oil soluble) component, i.e. tail, and a water soluble component, i.e. head. Examples of surfactants are polyoxyethylene products of hydrogenated vegetable oils, polyoxyethylene-sorbitan-fatty acid esters, and the like, for example, polyoxyethylene (50) hydrogenated castor oil which is commercialized under the trade mark Nikkol® (Nikkol HCO-50), polyoxyethylene (40) hydrogenated castor oil (Nikkol HCO-40), polyoxyethylene (60) hydrogenated castor oil (Nikkol HCO-60); polyoxyethylene (20) sorbitan monolaurate (polysorbate 20) which is commercialized under the trade mark Tween® (Tween 20), polysorbate 21 (Tween 21), polysorbate 40 (Tween 40), polysorbate 60 (Tween 60), polysorbate 80 (Tween 80), polysorbate 81 (Tween 81); sorbitan monooleate (Span 80); polyoxy-35-castoir oil (Cremophor® EL); polyoxyethylated glycerides (Labrafil® M2125 Cs), polyoxyethylated oleic glycerides (Labrafil® M1944 Cs); caprylocaproyl polyoxyl-8-glycerides (Labrasol®); D-α-tocopheryl polyethylene glycol 1000 succinate (TPGS).

The term "wax" refers a class of chemical compounds that are plastic (malleable) near room temperatures. Characteristically, they melt above 45° C. to give a low viscosity liquid. Waxes are insoluble in water but soluble in organic, nonpolar solvents. Waxes may contain esters of carboxylic acids and long chain alcohols or mixtures of substituted hydrocarbons, such as long chain fatty acids and primary alcohols (said substituted hydrocarbons having a hydrocarbon chain comprising more than 20 carbon atoms). Synthetic waxes are long-chain hydrocarbons lacking functional groups. Examples of waxes are synthetic wax, microcrystalline wax, paraffin wax, carnauba wax, beeswax, Chinese wax (insect wax), schellac wax, (lac wax), whale spermaceti, lanolin (wool wax), ouricuri wax, candelilla wax, esparto wax, ozocerite, and Montan wax.

Soft Capsules

In a first aspect, the present invention provides a soft capsule comprising:
a) a soft capsule shell; and
b) a pharmaceutical composition comprising:
  calcifediol,
  an oily component selected from the group consisting of medium chain triglyceride, isopropyl myristate, $C_{14}$-$C_{18}$ alkyl alcohol, $C_{14}$-$C_{18}$ alkenyl alcohol, lanolin alcohol and mixtures thereof, and
  a pharmaceutically acceptable organic solvent selected from the group consisting of ethanol, isopropanol, propylene glycol, polyethylene glycol, benzyl alcohol and mixtures thereof;
wherein the soft capsule shell encapsulates the pharmaceutical composition and wherein said pharmaceutical composition is devoid of waxes.

Preferably, the present invention provides a soft capsule comprising:
a) a soft capsule shell; and
b) a pharmaceutical composition comprising:
  calcifediol,
  an oily component selected from the group consisting of a medium chain triglyceride, isopropyl myristate, a $C_{14}$-$C_{18}$ alkenyl alcohol, and mixtures thereof, and
  a pharmaceutically acceptable organic solvent selected from the group consisting of ethanol, isopropanol, propylene glycol, polyethylene glycol, benzyl alcohol and mixtures thereof;
wherein the soft capsule shell encapsulates the pharmaceutical composition and wherein said pharmaceutical composition is devoid of waxes.

In one embodiment, the soft capsule shell comprises gelatin and a plasticizer selected from the group consisting of glycerol, sorbitol, propylene glycol, polyethylene glycol, dibutyl sebacate, diethyl phthalate, dimethyl phthalate, triacetin, tributyl citrate, triethyl citrate, and mixtures thereof; preferably a plasticizer selected form the group consisting of glycerol, sorbitol, and mixtures thereof.

The gelatins used for making soft capsules shells those approved by local authorities for pharmaceutical or nutritional use. These gelatins are mainly of two different types either alkaline (Type B) or acid (Type A) with medium gel strength (medium Bloom, such as 150-200 Bloom). Both types may be used in combination or separately. Preferably, a combination of gelatin type A and gelatin type B is used. Examples of type B gelatins are limed bone gelatins and limed hide gelatin. Examples of type A gelatins are pig skin gelatin, acid hide gelatin and fish gelatin.

In another embodiment, the soft capsule shell comprises:
  40 to 80 wt % of gelatin,
  10 to 50 wt % of plasticizer selected from the group consisting of glycerol, sorbitol, propylene glycol, polyethylene glycol, dibutyl sebacate, diethyl phthalate, dimethyl phthalate, triacetin, tributyl citrate, triethyl citrate, and mixtures thereof, preferably selected from the group consisting of glycerol, sorbitol and mixtures thereof, the amounts by weight being expressed with respect to the total weight of the soft capsule shell.

In a particular embodiment, the soft capsule shell comprises:
- 40 to 80 wt % of gelatin,
- 10 to 30 wt % of glycerol, and
- 5 to 15 wt % of sorbitol, the amounts by weight being expressed with respect to the total weight of the shell.

In another particular embodiment, the soft capsule shell comprises:
- 60 to 70 wt % of gelatin,
- 15 to 25 wt % of glycerol, and
- 5 to 15 wt % of sorbitol, the amounts by weight being expressed with respect to the total weight of the shell.

In one embodiment, the soft capsule shell further comprises a pharmaceutically acceptable opacifying agent and/or a pharmaceutically acceptable coloring agent. Opacifying agents are added to the soft capsule shell in order to make the shell opaque and thus protect the soft capsule filling, i.e. the pharmaceutical composition, from light. Suitable opacifying agents are known in the art and include titanium dioxide, talc, and the like. Coloring agents are added to the soft capsule shell to give the shell the desired color. Suitable coloring agents are known in the art and include sunset yellow FCF (E-110), indigo carmine (E-132), erythrosine (E-127), quinoline yellow (E-104), and the like.

In particular, the soft capsule shell has not been subjected to any cross-linking process.

The pharmaceutical composition encapsulated by the soft capsule shell comprises calcifediol; an oily component selected from the group consisting of medium chain triglyceride, isopropyl myristate, $C_{14}$-$C_{18}$ alkyl alcohol, $C_{14}$-$C_{18}$ alkenyl alcohol, lanolin alcohol and mixtures thereof; and a pharmaceutically acceptable organic solvent selected from the group consisting of ethanol, isopropanol, propylene glycol, polyethylene glycol, benzyl alcohol and mixtures thereof. Preferably, the pharmaceutical composition encapsulated by the soft capsule shell comprises calcifediol; an oily component selected from the group consisting of a medium chain triglyceride, isopropyl myristate, a $C_{14}$-$C_{18}$ alkenyl alcohol, and mixtures thereof; and a pharmaceutically acceptable organic solvent selected from the group consisting of ethanol, isopropanol, propylene glycol, polyethylene glycol, benzyl alcohol and mixtures thereof.

In one embodiment, the pharmaceutical composition of the soft capsule of the invention comprises:
- 0.001 to 0.2 wt % of calcifediol,
- 80 to 99.9 wt % of the oily component, and
- 0.3 to 6 wt % of the pharmaceutically acceptable organic solvent;

the amounts by weight being expressed with respect to the total weight of calcifediol, the oily component and the pharmaceutically acceptable organic solvent present in the pharmaceutical composition.

In one embodiment, the oily component is selected from a medium chain triglyceride, isopropyl myristate, a $C_{14}$-$C_{18}$ alkenyl alcohol, and mixtures thereof. In one embodiment, the oily component is selected from a medium chain triglyceride and isopropyl myristate, preferably a medium chain triglyceride, more preferably said medium chain triglyceride being caprylic/capric triglyceride.

In another embodiment the pharmaceutically acceptable organic solvent is selected from the group consisting of ethanol, isopropanol, propylene glycol, polyethylene glycol and mixtures thereof, preferably ethanol.

In one embodiment, the oily component is a medium chain triglyceride, preferably caprylic/capric triglyceride and/or the pharmaceutically acceptable organic solvent is selected from the group consisting of ethanol, isopropanol, propylene glycol, polyethylene glycol and mixtures thereof, preferably ethanol.

In a particular embodiment, the pharmaceutical composition of the soft capsule of the invention comprises:
- 0.001 to 0.2 wt % of calcifediol,
- 80 to 99.9 wt % of an oily component selected from the group consisting of a medium chain triglyceride (preferably caprylic/capric triglyceride) and isopropyl myristate, preferably a medium chain triglyceride (such as caprylic/capric triglyceride), and
- 0.3 to 6 wt % of a pharmaceutically acceptable organic solvent selected form the group consisting of ethanol, isopropanol, propylene glycol, polyethylene glycol and mixtures thereof, preferably ethanol, the amounts by weight being expressed with respect to the total weight of calcifediol, the oily component and the pharmaceutically acceptable organic solvent present in the pharmaceutical composition.

In a particular embodiment, the pharmaceutical composition of the soft capsule of the invention comprises:
- 0.001 to 0.1 wt % of calcifediol,
- 80 to 99.9 wt % of an oily component selected from the group consisting of a medium chain triglyceride (preferably caprylic/capric triglyceride) and isopropyl myristate, preferably a medium chain triglyceride (such as caprylic/capric triglyceride), and
- 0.5 to 5 wt % of a pharmaceutically acceptable organic solvent selected form the group consisting of ethanol, isopropanol, propylene glycol, polyethylene glycol and mixtures thereof, preferably ethanol, the amounts by weight being expressed with respect to the total weight of calcifediol, the oily component and the pharmaceutically acceptable organic solvent present in the pharmaceutical composition.

In another particular embodiment, the pharmaceutical composition of the soft capsule of the invention comprises:
- 0.001 to 0.1 wt % of calcifediol,
- 95 to 99.9 wt % of an oily component selected from the group consisting of a medium chain triglyceride (preferably caprylic/capric triglyceride) and isopropyl myristate, preferably a medium chain triglyceride (such as caprylic/capric triglyceride), and
- 0.5 to 1.5 wt % of a pharmaceutically acceptable organic solvent selected form the group consisting of ethanol, isopropanol, propylene glycol, polyethylene glycol and mixtures thereof, preferably ethanol, the amounts by weight being expressed with respect to the total weight of calcifediol, the oily component and the pharmaceutically acceptable organic solvent present in the pharmaceutical composition.

In another particular embodiment, the pharmaceutical composition of the soft capsule of the invention comprises:
- 0.01 to 0.1 wt % of calcifediol,
- 95 to 99.9 wt % of an oily component selected from the group consisting of a medium chain triglyceride (preferably caprylic/capric triglyceride) and isopropyl myristate, preferably a medium chain triglyceride (such as caprylic/capric triglyceride), and
- 0.5 to 1.5 wt % of a pharmaceutically acceptable organic solvent selected form the group consisting of ethanol, isopropanol, propylene glycol, polyethylene glycol and mixtures thereof, preferably ethanol, the amounts by weight being expressed with respect to the total weight of calcifediol, the oily component and the pharmaceutically acceptable organic solvent present in the pharmaceutical composition.

In a particular embodiment, the pharmaceutical composition of the soft capsule of the invention comprises:
0.01 to 0.5 mg of calcifediol,
400 to 500 mg of an oily component selected from the group consisting of a medium chain triglyceride (preferably caprylic/capric triglyceride) and isopropyl myristate, preferably a medium chain triglyceride (such as caprylic/capric triglyceride), and
2 to 20 mg of a pharmaceutically acceptable organic solvent selected form the group consisting of ethanol, isopropanol, propylene glycol, polyethylene glycol and mixtures thereof, preferably ethanol.

In another particular embodiment, the pharmaceutical composition of the soft capsule of the invention comprises:
0.01 to 0.5 mg of calcifediol,
400 to 500 mg of a caprylic/capric triglyceride, and
4 to 6 mg of ethanol, 5 to 10 mg polyethylene glycol, and/or 2 to 8 mg propylene glycol, preferably 4 to 6 mg of ethanol.

In another particular embodiment, the pharmaceutical composition of the soft capsule of the invention comprises:
0.2 to 0.4 mg of calcifediol,
400 to 500 mg of isopropyl myristate, and
4 to 6 mg of ethanol.

In another particular embodiment, the pharmaceutical composition of the soft capsule of the invention comprises:
0.2 to 0.4 mg of calcifediol,
400 to 500 mg of isopropyl myristate,
3 to 6 mg of ethanol, and
10 to 25 mg polyethylene glycol or propylene glycol.

In a further embodiment, the pharmaceutical composition of the soft capsule of the invention further comprises calcium or a pharmaceutically acceptable derivative thereof, preferably calcium ions ($Ca^{2+}$). Calcium and pharmaceutically acceptable derivatives thereof refers to any pharmaceutically acceptable source of calcium or calcium ions, such as pharmaceutically acceptable calcium salts, calcium hydroxide and hydroxyapatite. Examples of said pharmaceutically acceptable calcium salts are calcium carbonate, chloride, chloride hexahydrate, citrate, formate, glycinate, bisglycinate, glucoheptonate, gluconate, gluconolactate, glutamate, glycerophosphate, hydrogenophosphate, lactate, lactobionate, lactophosphate, levulinate, oleate, monobasic or tribasic phosphate, pidolate, sulfate. Preferably, the calcium or calcium ion is provided as calcium glycinate, calcium bisglycinate, calcium hydroxide or mixtures thereof. More preferably, the calcium or calcium ion is provided as calcium glycinate, calcium bisglycinate, or mixtures thereof.

In a further embodiment, the pharmaceutical composition of the soft capsule of the invention comprises calcium or a pharmaceutically acceptable derivative thereof; iron or a pharmaceutically acceptable derivative thereof; vitamin B12; vitamin B9 (also known as folic acid or folate); levomefolic acid or a pharmaceutically acceptable salt thereof; and/or essential unsaturated fatty acids or mixtures thereof.

Iron and derivatives thereof refers to any pharmaceutically acceptable source of iron, such as iron ions ($Fe^{2+}$ and/or $Fe^{3+}$), which may be provided as pharmaceutically acceptable iron salts; and elemental iron, which may be provided as a metalloprotein or as a coordination complex, wherein the iron (Fe(III) or Fe(II)) is coordinated by nitrogen, oxygen or sulfur centres belonging to amino acid residues of a protein or another pharmaceutically acceptable organic compound. Examples of said pharmaceutically acceptable iron salts are ferrous salts and ferric salts, preferably such as ferric ammonium citrate, ferric phosphate, ferric pyrophosphate, ferritin, ferrocholinate, ferrous ascorbate, ferrous aspartate, ferrous chloride, ferrous sulfate, ferrous tartrate, ferrous fumarate, ferrous gluconate, ferrous gluceptate, ferrous glycine sulfate, ferrous lactate, ferrous oxalate and ferrous succinate. Examples of said iron metalloproteins or coordination complexes are iron glycinate complex, iron glucose complex, iron fructose complex, iron polymaltose complex, and iron sucrose complex.

In a particular embodiment, the pharmaceutical composition of the soft capsule of the invention comprises:
calcifediol,
a medium chain triglyceride, preferably caprylic/capric triglyceride,
ethanol, and
calcium or a pharmaceutically acceptable derivative thereof.

In another particular embodiment, the pharmaceutical composition of the soft capsule of the invention comprises:
calcifediol,
a medium chain triglyceride, preferably caprylic/capric triglyceride,
ethanol,
calcium or a pharmaceutically acceptable derivative thereof,
iron or a pharmaceutically acceptable derivative thereof,
vitamin B12,
vitamin B9, levomefolic acid or a pharmaceutically acceptable salt thereof, and
an essential unsaturated fatty acid.

In one embodiment, the pharmaceutical composition of the soft capsule of the invention further comprises a bisphosphonate. Bisphosphonates are well known in the art as a class of drugs that prevent the loss of bone mass and have two phosphonate groups. Preferably the bisphosphonate is selected form the group consisting of alendronic acid, risedronic acid, ibandronic acid, clodronic acid, tiludronic acid, etidronic acid, pamidronic acid, zoledronic acid and mixtures thereof; more preferably the bisphosphonate is selected from the group consisting of alendronic acid, ibandronic acid and mixtures thereof.

In another preferred embodiment the pharmaceutical composition of the soft capsule contains less than 10% of water. Preferably less than 5%, more preferably less than 2.5%, even more preferably 1%, and most preferably less than 0.5% of water.

In a particular embodiment, the pharmaceutical composition of the soft capsule of the invention comprises:
calcifediol,
a medium chain triglyceride, preferably caprylic/capric triglyceride,
ethanol, and
a bisphosphonate, preferably a alendronic acid, ibandronic acid or mixture thereof.

Surprisingly, the soft capsule of the invention forms SEDDS in the absence of a surfactant, which is known to be one of the essential components of these type of systems. Thus, in a preferred embodiment, the soft capsule of the invention is devoid of surfactants.

In another preferred embodiment, the soft capsule is devoid of a cellulose polymer. Examples of cellulose polymers are methylcellulose, hydroxyethyl cellulose, hydroxypropyl cellulose, hydroxypropyl methylcellulose, hydroxypropyl ethylcellulose, and sodium carboxymethylcellulose.

The pharmaceutical composition encapsulated in the soft capsule of the present invention may further comprise pharmaceutically acceptable excipients. The term "pharmaceutically acceptable excipient" refers to a vehicle, diluent, or adjuvant that is administered with the active ingredient. Conventional pharmaceutically acceptable excipients are known by the skilled person. For example, suitable pharmaceutical excipients are described in "Remington's Pharmaceutical Sciences" by E. W. Martin, 21st Edition, 2005.

In particular, the pharmaceutical composition encapsulated in the soft capsule of the present invention is a liquid composition.

The amount of calcifediol in the soft capsule of the invention is preferably comprised in the range of from 200 to 180,000 IU of calcifediol.

In one embodiment, the soft capsule of the invention provides a $C_{max}$ of calcifediol at least 1.2 times greater than the $C_{max}$ of an equivalent amount of calcifediol administered as an oral liquid preparation containing calcifediol, a medium chain triglyceride and α-tocopherol acetate, preferably at least 1.25 times greater, more preferably at least 1.3 times greater, more preferably 1.35 times greater.

In another embodiment, the soft capsule of the invention provides an $AUC_{0-72}$ at least 1.2 times greater than the $AUC_{0-72}$ of an equivalent amount of calcifediol administered as an oral liquid preparation containing calcifediol, a medium chain triglyceride and α-tocopherol acetate, preferably at least 1.25 times greater.

In a further embodiment, the soft capsule of the invention provides a $C_{max}$ of calcifediol at least 1.2 times greater than the $C_{max}$ of an equivalent amount of calcifediol administered as an oral liquid preparation containing calcifediol, a medium chain triglyceride and α-tocopherol acetate, preferably at least 1.25 times greater, more preferably at least 1.3 times greater, more preferably 1.35 times greater; and an $AUC_{0-72}$ at least 1.2 times greater than the $AUC_{0-72}$ of an equivalent amount of calcifediol administered as an oral liquid preparation containing calcifediol, a medium chain triglyceride and a-tocopherol acetate, preferably at least 1.25 times greater.

The $C_{max}$ and $AUC_{0-72}$ are determined using standard procedures in the art, in accordance with Directive 2001/20/EC. In particular these parameters are determined by administering calcifediol, removing blood samples (3 ml) at basal time (e.g. the mean value obtained at −0.5 h, −0.25 h and 0 h) and after administration of calcifediol (e.g. at 2, 4, 4.5, 5, 5.5, 6, 6.5, 7, 8, 10, 12, 24, 48 and 72 h). The plasmatic concentration of calcifediol in the blood samples is determined by means of HPLC-MS; the $C_{max}$ corresponds to the maximum calcifediol concentration observed, and the $AUC_{0-72}$ is determined by integration of the area under the plot of concentration of drug in blood plasma against time by common mathematical procedures, such as by the trapezoidal rule.

The reference oral liquid preparation containing calcifediol, a medium chain triglyceride and α-tocopherol acetate is that marketed by Faes Farma under the name Hidroferol®, wherein calcifediol is provided as an ampoule comprising a solution consisting of calcifediol (such as 0.266 mg; 15,960 IU calcifediol; or an amount equivalent to calcifediol in the soft capsule according to the present invention), medium chain triglycerides (1.5 ml) and α-tocopherol acetate (0.266 mg; vitamin E acetate). The presence of linearity in the dose range of calcifediol (between 0.105 mg and 0.700 mg) (Haddad J G Jr, Rojanasathit S. Acute administration of 25-hydroxycholecalciferol in man. *J Clin Endocrinol Metab*. 1976; 42(2):284-90, allows a study dose of 0.532 mg (2×0.266 mg) in order to obtain an adequate separation in exposure ensuring that the comparison is sensitive to detect potential differences between formulations.

Medical Uses of the Soft Capsules

Calcifediol has been described for use in the treatment of diseases related to vitamin D deficiency.

Thus, in a further aspect, the present invention relates to a soft capsule as defined above for use in medicine.

A further aspect of the invention is a soft capsule as defined above, for use in the treatment and/or prevention of a disease selected from the group consisting of vitamin D deficiency, demineralization such as hypocalcemia and hypophosphatemia, renal osteodystrophy, rickets, osteoporosis, osteopenia, osteoarthritis, osteoarthrosis, osteomalacia, hypoparathyroidism, and inflammatory bowel disease.

A further aspect of the invention is directed to the use of a soft capsule as defined above, in the manufacture of a medicament for the treatment and/or prevention of a disease selected from the group consisting of vitamin D deficiency, demineralization such as hypocalcemia and hypophosphatemia, renal osteodystrophy, rickets, osteoporosis, osteopenia, osteoarthritis, osteoarthrosis, osteomalacia, hypoparathyroidism, and inflammatory bowel disease.

In a further aspect, the invention is directed to a method of treatment and/or prevention of a disease selected from the group consisting of vitamin D deficiency, demineralization such as hypocalcemia and hypophosphatemia, renal osteodystrophy, rickets, osteoporosis, osteopenia, osteoarthritis, osteoarthrosis, osteomalacia, hypoparathyroidism, and inflammatory bowel disease, said method comprising administering to a patient in need of such a treatment a soft capsule as described above.

The term "treatment" or "to treat" in the context of this specification means administration of a compound or formulation according to the invention to ameliorate or eliminate the disease or one or more symptoms associated with said disease. "Treatment" also encompasses ameliorating or eliminating the physiological sequelae of the disease.

The term "ameliorate" in the context of this invention is understood as meaning any improvement on the situation of the patient treated.

The term "prevention" or "to prevent" refer to the reduction in the risk of acquiring or developing a given disease or disorder, or the reduction or inhibition of the recurrence or a disease or disorder.

In particular, the soft capsule for use as defined above is for administration once every three months, once every two months, once a month, once every three weeks, once every two weeks, once a week, or once a day. Preferably, the soft capsule for administration once every three months comprises from 24000 IU to 16000 IU of calcifediol. Preferably, the soft capsule for administration once every two months comprises from 24000 IU to 16000 IU of calcifediol. Preferably, the soft capsule for administration once a month comprises from 24000 IU to 16000 IU of calcifediol. Preferably, the soft capsule for administration once every three weeks comprises from 16000 IU to 14000 IU of calcifediol. Preferably, the soft capsule for administration once every two weeks comprises from 14000 IU to 12000 IU of calcifediol. Preferably, the soft capsule for administration once a week comprises from 10000 IU to 8000 IU of calcifediol, more preferably 9000 IU of calcifediol. Preferably, the soft capsule for administration once a day comprises from 1000 IU to 400 IU of calcifediol.

In particular, the soft capsule for use as defined above, wherein the pharmaceutical composition comprised in said soft capsule additionally comprises a bisphosphonate; preferably a bisphosphonate selected form the group consisting of alendronic acid, risedronic acid, ibandronic acid, clodronic acid, tiludronic acid, etidronic acid, pamidronic acid, zoledronic acid and mixtures thereof; more preferably a bisphosphonate selected from the group consisting of alendronic acid, ibandronic acid and mixtures thereof. Said soft capsule for use as defined above, is for administration once a month or once a week. Preferably, the soft capsule for administration once a month comprises from 24000 IU to 16000 IU of calcifediol and 150 mg ibandronic acid. Preferably, the soft capsule for administration once a week comprises from 2800 IU to 5600 IU of calcifediol and 70 mg alendronic acid. Said soft capsules are particularly useful for the treatment and/or prevention of osteoarthritis and/or osteoarthrosis.

Process for Preparing the Soft Capsules

The soft capsules of the present invention can be prepared by any conventional manufacturing process known in the art for the preparation of soft capsules (as described for example in Gurava reddy, R. et al., *Int. J. Adv. Pharm. Gen. Res.*, 2013, 1, 20-29), such as by a rotary-die process.

In particular, a further aspect of the present invention relates to a process form preparing a soft capsule as defined above, said process comprising:

a) preparing a mixture comprising calcifediol; the oily component; and the pharmaceutically acceptable organic solvent; and optionally calcium or a pharmaceutically acceptable derivative thereof, iron or a pharmaceutically acceptable derivative thereof, vitamin B12, vitamin B9, levomefolic acid or a pharmaceutically acceptable salt thereof, an essential unsaturated fatty acid and/or a bisphosphonate;

b) preparing a mixture comprising gelatin; the plasticizer; water; and optionally a pharmaceutically acceptable opacifying agent and/or a pharmaceutically acceptable coloring agent;

c) forming a shell from the mixture of step b);

d) filling the shell with the mixture of step a), and e) drying the capsule obtained in step d).

Step a) comprises preparing a mixture comprising the ingredients that will be present in the pharmaceutical composition encapsulated by the soft capsule shell, i.e. calcifediol, the oily component, and the pharmaceutically acceptable organic solvent. Preferably, said mixture is a solution. Additionally, if further ingredients are present in said pharmaceutical composition, such as calcium or a pharmaceutically acceptable derivative thereof, iron or a pharmaceutically acceptable derivative thereof, vitamin B12, vitamin B9, levomefolic acid or a pharmaceutically acceptable salt thereof, an essential unsaturated fatty acid, and/or a bisphosphonate, said ingredients are also included in the mixture of step a). Preferably, said mixture is prepared by dissolving calcifediol in the pharmaceutically acceptable organic solvent and then adding the solution thus obtained to the oily components, any additional ingredient that will be present in the pharmaceutical composition are also added to the oily component. Preferably, step a) is carried out under an inert atmosphere such as under a nitrogen atmosphere.

Step b) comprises preparing an aqueous mixture of the ingredients that will form the soft capsule shell, i.e. gelatin and plasticizer; and any additional ingredients that can be present such as a pharmaceutically acceptable opacifying agent and/or a pharmaceutically acceptable coloring agent. Preferably, said mixture is a solution.

Steps a) can be performed before step b), step b) can be performed before step a), or steps a) and b) can be performed simultaneously.

Step c) comprises forming a shell from the mixture of step b), and step d) comprises filling the shell with the mixture of step a). Preferably, steps c) and d) are carried out simultaneously, for example by use of rotary die technology which begins with the formation of two plasticized films called ribbons from the mixture of step b), each ribbon is then passed over a die and sealed to the other ribbon at the point where the two rotary meet while filled with the mixture of step a). In a particular embodiment, step c) and/or step d) are carried out under controlled relative humidity (RH) conditions, such as 20% to 40% RH, preferably 25% to 35% RH, more preferably 30% RH.

Finally, step e) comprises drying the capsule obtained in the previous step, generally down to about 6% remaining water, for example in tumble dryer and tunnel dryer. In a particular embodiment, step e) is carried out under controlled relative humidity (RH) conditions, such as 10% to 30% RH, preferably 15% to 25% RH, more preferably 22% RH.

The present invention will be more specifically illustrated by the following examples. However, it should be understood that the present invention is not limited by these examples in any manner.

EXAMPLES

Example 1. Calcifediol Soft Capsules a) Soft Capsule Shell

| | |
|---|---|
| Gelatin (type A/B, Gelita) | 147.937 mg |
| Sorbitol (70% v/v) | 31.302 mg |
| Glicerol | 46.096 mg |
| Titanium dioxide | 3.098 mg |
| Sunset yellow E-110 | 0.958 mg |
| Water* | q.s. |

*evaporated when drying the capsule b) Pharmaceutical Compositions

Pharmaceutical Composition 1

| | |
|---|---|
| Calcifediol | 0.266 mg |
| Mygliol ® 812* | 494.5 mg |
| Absolute ethanol | 4.98-5.24 mg |

*caprylic/capric triglyceride

Pharmaceutical Composition 2:

| | |
|---|---|
| Calcifediol | 0.266 mg |
| Mygliol ® 812* | 400-480 mg |
| Absolute ethanol | 3-6 mg |
| PEG400 | 5-10 mg |

*caprylic/capric triglyceride

Pharmaceutical Composition 3:

| | |
|---|---|
| Calcifediol | 0.266 mg |
| Isopropyl myristate | 400-480 mg |
| Absolute ethanol | 3-6 mg |

Pharmaceutical Composition 4:

| | |
|---|---|
| Calcifediol | 0.266 mg |
| Mygliol ® 812* | 400-480 mg |
| Propylene glycol | 2-8 mg |

*caprylic/capric triglyceride

Soft Capsule Preparation:
1. Calcifediol is dissolved in the pharmaceutically acceptable organic solvent.
2. The solution of step 1 is added to the oily component under a nitrogen atmosphere.
3. The mixture of soft capsule shell components is prepared by providing water, heating at 75° C., adding glycerol and sorbitol, heating at 75° C., adding gelatin, mixing by vacuum and heat, adding sunset yellow and titanium dioxide, and mixing.
4. The mixture obtained in step 2 is dosified in soft capsules by forming a soft capsule shell with the mixture of step 3.

Example 2. Reference Calcifediol Formulation

Reference calcifediol formulation was Hidroferol® (Faes Farma) which is a solution of calcifediol packaged in ampoules comprising:

| | |
|---|---|
| Calcifediol | 0.266 mg |
| α-tocopherol acetate (Vitamin E acetate) | 0.266 mg |
| Massocare ® MCT* | 1.5 ml |

*caprylic/capric triglyceride

Example 3. Pharmacokinetic Studies

HPCL Method
General Description:
The method involved a liquid-liquid extraction procedure with n-pentane and subsequent derivatization with 4-phenyl-1,2,4-triazoline-3,5-dione (PTAD). Calcifediol and internal standard were measured by reversed phase high performance liquid chromatography coupled to a tandem mass spectrometry detector (LC/MS/MS).
Equipment
Instrumental System:
The modular liquid chromatographic system was made up of: an HTC autosampler (CTC-PAL), a high pressure binary pump (Agilent 1200 Series), a high pressure pump (Perkin Elmer series 200), a mass spectrometer detector API 4000 (MDS Sciex), a column heater (CROCO-CIL) and a 10-port switching valve (VICI).
Data acquisition and data integration were done using MDS Sciex Analyst version 1.4.2 software.
Chromatographic Conditions:
Separations were performed on a reversed-phase column (Unison UK-C18, 2×50 mm, 3 μm, from Imtakt). Mobile phase A was methylamine 1 mM, 0.1% formic acid prepared in water and mobile phase B was methylamine 1 mM, 0.1% formic acid prepared in methanol. The chromatographic separation was gradiently performed at 40° C. at a flow-rate ranged between 0.5 to 1.00 mL/min.
Detection Conditions:
calcifediol 607.5→298.0 amu
calcifediol-d6 (Internal Standard) 613.5→298.0 amu Extraction Method:
100 μL of internal standard working solution were transferred into tubes containing 100 μL of plasma from each sample (study sample, calibration standard or quality control) and then it was extracted with n-pentane. Subsequently, it was derivatized with PTAD
Pharmacokinetic Study
A randomized, two-stage, two-sequence, two-period, crossover clinical trial to compare the bioavailability of a soft capsule of Example 1 comprising the pharmaceutical composition 1 (calcifediol soft capsule) with respect to the reference calcifediol formulation of Example 2 (calcifediol ampoule) after single dose administration to healthy volunteers under fasting conditions was carried out.
72 volunteers (38 men and 34 women) of 18 to 35 years old were randomly distributed in two groups, groups A and B. In a first period (P1: 6 days) group A received two calcifediol ampoules, whereas group B received two calcifediol soft capsules. After a washing period of at least 105 days, group A received two calcifediol soft capsules and group B received two calcifediol ampoules during a second period P2 (8 days). To volunteers abandoned the trial before the second period P2 due to personal reasons. Finally, 70 volunteers (36 men and 34 women) concluded the study.
$C_{max}$ and $AUC_{0-72}$ are determined by measuring the plasmatic concentration of calcifediol in blood samples using HPLC-MS as described above. Blood samples (3 ml) were taken at basal time (the mean value obtained at −0.5 h, −0.25 h and 0 h) and after administration of the calcifediol formulation, either as soft capsules or as ampoules, at 2, 4, 4.5, 5, 5.5, 6, 6.5, 7, 8, 10, 12, 24, 48 and 72 h). The time-plasmatic concentration plot is shown in FIG. 1. $C_{max}$ and $AUC_{0-72}$ were obtained from the time-plasmatic concentration plots using WinNonlin 6.3 software (Pharsight Corporation, Cary USA). The results are shown in the table below as the mean value±standard deviation (SD).

| Parameter | Calcifediol ampoules | Calcifediol soft capsules |
|---|---|---|
| $C_{max}$ (ng/ml) | 41.46 ± 15.42 | 56.44 ± 18.15 |
| $AUC_{0-72}$ (ng/ml · h) | 1877.05 ± 596.56 | 2382.02 ± 665.43 |

The invention claimed is:
1. A soft capsule comprising:
a) a soft capsule shell; and
b) a pharmaceutical composition comprising:
calcifediol,
an oily component selected from the group consisting of a medium chain triglyceride, isopropyl myristate, a $C_{14}$-$C_{18}$ alkyl alcohol, a $C_{14}$-$C_{18}$ alkenyl alcohol, lanolin alcohol, and mixtures thereof, and
a pharmaceutically acceptable organic solvent selected from the group consisting of ethanol, isopropanol, propylene glycol, polyethylene glycol, benzyl alcohol, and mixtures thereof;
wherein the soft capsule shell encapsulates the pharmaceutical composition and wherein said pharmaceutical composition is devoid of waxes, wherein the soft capsule shell comprises:
40 to 80 wt % of gelatin,
10 to 50 wt % of plasticizer selected from the group consisting of glycerol, sorbitol, propylene glycol, polyethylene glycol, dibutyl sebacate, diethyl phthalate, dimethyl phthalate, triacetin, tributyl citrate, triethyl citrate, and mixtures thereof,
the amounts by weight being expressed with respect to the total weight of the soft capsule shell; and/or wherein the pharmaceutical formulation comprises:
   0.001 to 0.2 wt % of calcifediol,
   95 to 99.9 wt % of the oily component, and
   0.3 to 6 wt % of the pharmaceutically acceptable organic solvent;
the amounts by weight being expressed with respect to the total weight of calcifediol, the oily component, and the pharmaceutically acceptable organic solvent present in the pharmaceutical composition, wherein the weight percentages of calcifediol, the oily component, and the pharmaceutically acceptable organic solvent, total to 100 wt %;
and wherein the soft capsule provides a $C_{max}$ of calcifediol at least 1.2 times greater than the $C_{max}$ of an equivalent amount of calcifediol administered as an oral liquid preparation containing calcifediol.

2. Soft capsule according to claim 1, wherein the oily component is selected from the group consisting of a medium chain triglyceride, isopropyl myristate, a $C_{14}$-$C_{18}$ alkenyl alcohol, and mixtures thereof.

3. Soft capsule according to claim 1, wherein the oily component is a medium chain triglyceride and/or wherein the pharmaceutically acceptable organic solvent is selected from the group consisting of ethanol, isopropanol, propylene glycol, polyethylene glycol and mixtures thereof.

4. Soft capsule according to claim 1, wherein the oily component is caprylic/capric triglyceride, and/or wherein the pharmaceutically acceptable organic solvent is selected from the group consisting of ethanol, isopropanol, propylene glycol, polyethylene glycol and mixtures thereof.

5. Soft capsule according to claim 1, wherein the oily component is caprylic/capric triglyceride, and/or wherein the pharmaceutically acceptable organic solvent is ethanol.

6. Soft capsule according to claim 1, which is devoid of surfactants.

7. Soft capsule according to claim 1, wherein the pharmaceutical composition further comprises calcium or a pharmaceutically acceptable derivative thereof.

8. Soft capsule according to claim 1, wherein the pharmaceutical composition further comprises iron or a pharmaceutically acceptable derivative thereof, vitamin B12, vitamin B9, levomefolic acid or a pharmaceutically acceptable salt thereof, and/or an essential unsaturated fatty acid, or mixtures thereof.

9. Soft capsule according to claim 1, wherein the pharmaceutical composition further comprises a bisphosphonate.

10. Soft capsule according to claim 1, wherein the soft capsule shell further comprises a pharmaceutically acceptable opacifying agent and/or a pharmaceutically acceptable coloring agent.

11. Soft capsule according to claim 1 comprising from 200 to 180000 IU of calcifediol.

12. Method of treatment and/or prevention of a disease related to vitamin D deficiency, said method comprising administering to a patient in need of such a treatment a therapeutically effective amount of a soft capsule as defined in claim 1.

13. Method of treatment and/or prevention of a disease selected from the group consisting of vitamin D deficiency, demineralization, renal osteodystrophy, rickets, osteoporosis, osteopenia, osteoarthritis, osteoarthrosis, osteomalacia, hypoparathyroidism, and inflammatory bowel disease, said method comprising administering to a patient in need of such a treatment a therapeutically effective amount of a soft capsule as defined in claim 1.

14. Method of treatment and/or prevention of a disease selected from the group consisting of vitamin D deficiency, hypocalcemia and hypophosphatemia, renal osteodystrophy, rickets, osteoporosis, osteopenia, osteoarthritis, osteoarthrosis, osteomalacia, hypoparathyroidism, and inflammatory bowel disease, said method comprising administering to a patient in need of such a treatment a therapeutically effective amount of a soft capsule as defined in claim 1.

15. Method according to claim 13, wherein the soft capsule is for administration once every three months, once every two months, once a month, once every three weeks, once every two weeks, once a week, or once a day.

16. A process for preparing a soft capsule as defined in claim 1, said process comprising:
   a) preparing a mixture comprising calcifediol; the oily component; and the pharmaceutically acceptable organic solvent;
   b) preparing a mixture comprising gelatin; the plasticizer; and water;
   c) forming a shell from the mixture of step b);
   d) filling the shell with the mixture of step a), and
   e) drying the capsule obtained in step d).

17. The process of claim 16, wherein the mixture comprising calcifediol; the oily component; and the pharmaceutically acceptable organic solvent in step (a) further comprises calcium or a pharmaceutically acceptable derivative thereof; iron or a pharmaceutically acceptable derivative thereof; vitamin B12; vitamin B9; levomefolic acid or a pharmaceutically acceptable salt thereof; an essential unsaturated fatty acid; and/or bisphosphonate.

18. The process of claim 16, wherein the mixture comprising gelatin; the plasticizer; and water in step (b) further comprises a pharmaceutically acceptable opacifying agent and/or a pharmaceutically acceptable coloring agent.

19. A soft capsule according to claim 1, wherein the soft capsule shell encapsulates the pharmaceutical composition and wherein said pharmaceutical composition is devoid of waxes, wherein the soft capsule shell comprises:
   40 to 80 wt % of gelatin,
   10 to 50 wt % of plasticizer selected from the group consisting of glycerol, sorbitol, propylene glycol, polyethylene glycol, dibutyl sebacate, diethyl phthalate, dimethyl phthalate, triacetin, tributyl citrate, triethyl citrate, and mixtures thereof,
the amounts by weight being expressed with respect to the total weight of the soft capsule shell.

20. A soft capsule according to claim 1, wherein the pharmaceutical formulation comprises:
   0.001 to 0.2 wt % of calcifediol,
   95 to 99.9 wt % of the oily component, and
   0.3 to 6 wt % of the pharmaceutically acceptable organic solvent;
the amounts by weight being expressed with respect to the total weight of calcifediol, the oily component and the pharmaceutically acceptable organic solvent present in the pharmaceutical composition, wherein the weight percentages of calcifediol, the oily component, and the pharmaceutically acceptable organic solvent, total to 100 wt %.

21. Soft capsule according to claim 1, wherein the soft capsule shell comprises 60 to 70 wt. % of gelatin, based on the total weight of the soft capsule shell.

22. Soft capsule according to claim 19, wherein the soft capsule shell comprises 60 to 70 wt. % of gelatin, based on the total weight of the soft capsule shell.

23. Soft capsule according to claim 1, wherein the soft capsule shell comprises 60 to 70 wt. % of gelatin, 15 to 25 wt. % of glycerol, and 5 to 15 wt. % of sorbitol, based on the total weight of the soft capsule shell.

24. The process of claim 16, wherein the mixture of b) comprises gelatin, glycerol, sorbitol, and water.

25. The process of claim 18, wherein the mixture of b) comprises gelatin, glycerol, sorbitol, and water.

26. Soft Capsule according to claim 19, wherein the soft capsule shell comprises 60 to 70 wt. % of gelatin, 15 to 25 wt. % of glycerol, and 5 to 15 wt. % of sorbitol, based on the total weight of the soft capsule shell.

27. A soft capsule, comprising:
a) a soft capsule shell; and
b) a pharmaceutical composition comprising:
  calcifediol,
  an oily component selected from the group consisting of a medium chain triglyceride, isopropyl myristate, a $C_{14}$-$C_{18}$ alkyl alcohol, a $C_{14}$-$C_{18}$ alkenyl alcohol, lanolin alcohol, and mixtures thereof, and
  a pharmaceutically acceptable organic solvent selected from the group consisting of ethanol, isopropanol, propylene glycol, polyethylene glycol, benzyl alcohol, and mixtures thereof;
wherein the soft capsule shell encapsulates the pharmaceutical composition and wherein said pharmaceutical composition is devoid of waxes, wherein the soft capsule shell comprises:
  40 to 80 wt % of gelatin,
  10 to 50 wt % of plasticizer selected from the group consisting of glycerol, sorbitol, propylene glycol, polyethylene glycol, dibutyl sebacate, diethyl phthalate, dimethyl phthalate, triacetin, tributyl citrate, triethyl citrate, and mixtures thereof,
  the amounts by weight being expressed with respect to the total weight of the soft capsule shell;
and
wherein the pharmaceutical formulation comprises:
  0.001 to 0.2 wt % of calcifediol,
  80 to 99.9 wt % of the oily component, and
  0.3 to 6 wt % of the pharmaceutically acceptable organic solvent;
  the amounts by weight being expressed with respect to the total weight of calcifediol, the oily component, and the pharmaceutically acceptable organic solvent present in the pharmaceutical composition, wherein the weight percentages of calcifediol, the oily component, and the pharmaceutically acceptable organic solvent, total to 100 wt %;
and wherein the soft capsule shell provides a $C_{max}$ of calcifediol at least 1.2 times greater than the $C_{max}$ of an equivalent amount of calcifediol administered as an oral liquid preparation containing calcifediol.

28. The soft capsule according to claim 27, wherein the soft capsule shell comprises 60 to 70 wt % of gelatin, and 15 to 25 wt % of glycerol, based on the total weight of the soft capsule shell.

29. The soft capsule according to claim 27, wherein the pharmaceutical formulation comprises 95 to 99.9 wt % of the oily component.

* * * * *

UNITED STATES PATENT AND TRADEMARK OFFICE
CERTIFICATE OF CORRECTION

PATENT NO. : 10,525,018 B2  
APPLICATION NO. : 15/524174  
DATED : January 7, 2020  
INVENTOR(S) : Josep Maria Sune Negre Page 1 of 1

It is certified that error appears in the above-identified patent and that said Letters Patent is hereby corrected as shown below:

On the Title Page

Under (30) Foreign Application Priority Data:  
"(EP)..................15382042" should be -- (EP)..................15382042.8 --.

Signed and Sealed this  
Eighteenth Day of February, 2020

Andrei Iancu  
*Director of the United States Patent and Trademark Office*